(12) United States Patent
Tucker et al.

(10) Patent No.: US 9,526,808 B2
(45) Date of Patent: *Dec. 27, 2016

(54) AIR FRESHENING DEVICE

(75) Inventors: Christopher S. Tucker, Midlothian, VA (US); Walter A. Nichols, Chesterfield, VA (US)

(73) Assignee: Philip Morris USA Inc., Richmond, VA (US)

( * ) Notice: Subject to any disclaimer, the term of this patent is extended or adjusted under 35 U.S.C. 154(b) by 598 days.

This patent is subject to a terminal disclaimer.

(21) Appl. No.: 12/903,419

(22) Filed: Oct. 13, 2010

(65) Prior Publication Data

US 2011/0253798 A1  Oct. 20, 2011

Related U.S. Application Data (60) Provisional application No. 61/251,189, filed on Oct. 13, 2009.

(51) Int. Cl.
*A61L 9/03* (2006.01)
*A61L 9/14* (2006.01)

(52) U.S. Cl.
CPC ........ *A61L 9/037* (2013.01); *A61L 9/14* (2013.01); *A61L 2209/11* (2013.01); *A61L 2209/135* (2013.01)

(58) Field of Classification Search
CPC  A61L 2209/11; A61L 2209/135; A61L 9/037; A61L 9/14
USPC ....... 392/394–398; 122/366; 239/44, 45, 47, 239/49, 57
See application file for complete search history.

(56) References Cited

U.S. PATENT DOCUMENTS

| | | | |
|---|---|---|---|
| 4,020,321 | A | 4/1977 | Oswald |
| 4,676,237 | A | 6/1987 | Wood et al. |
| 4,740,366 | A | 4/1988 | Winston et al. |
| 5,011,632 | A | 4/1991 | Yano et al. |
| 5,095,647 | A | 3/1992 | Zobele et al. |
| 5,196,171 | A | 3/1993 | Peltier |
| 5,221,025 | A | 6/1993 | Privas |
| 5,290,546 | A | 3/1994 | Hasegawa et al. |

(Continued)

FOREIGN PATENT DOCUMENTS

| | | |
|---|---|---|
| EP | 0897755 A2 | 2/1999 |
| EP | 1762253 A2 | 3/2007 |

(Continued)

OTHER PUBLICATIONS

International Search Report and Written Opinion mailed May 28, 2009 for PCT/IB2008/003020.

(Continued)

*Primary Examiner* — David Angwin
*Assistant Examiner* — Frederick Calvetti
(74) *Attorney, Agent, or Firm* — Buchanan Ingersoll & Rooney PC (57) ABSTRACT

An air freshening device includes a liquid supply operable to supply liquid fragrance material, a wick in contact with the liquid supply, a conductive mesh material operable to retain the liquid material in interstices thereof, and a power supply operable to apply voltage across the mesh material so as to heat the mesh material and the liquid fragrance material contained in interstices of the mesh material to a temperature sufficient to vaporize the liquid. The air freshening device is operable to substantially prevent deposition of the vaporized liquid material.

24 Claims, 7 Drawing Sheets

(56) References Cited

U.S. PATENT DOCUMENTS

| | | |
|---|---|---|
| 5,382,410 A | 1/1995 | Peltier |
| 5,484,086 A | 1/1996 | Pu |
| 5,591,409 A | 1/1997 | Watkins |
| 5,647,053 A | 7/1997 | Schroeder et al. |
| 5,743,251 A | 4/1998 | Howell et al. |
| 5,972,290 A | 10/1999 | De Sousa |
| 6,155,268 A | 12/2000 | Takeuchi |
| 6,236,807 B1 | 5/2001 | Ruffolo et al. |
| 6,238,646 B1 | 5/2001 | Zembrodt |
| 6,293,474 B1 | 9/2001 | Helf et al. |
| 6,296,196 B1 | 10/2001 | Denen et al. |
| 6,325,475 B1 | 12/2001 | Hayes et al. |
| 6,361,752 B1 | 3/2002 | Demarest et al. |
| 6,378,780 B1 | 4/2002 | Martens, III et al. |
| 6,386,462 B1 | 5/2002 | Martens, III |
| 6,412,494 B1 | 7/2002 | Bloom, Jr. |
| 6,439,474 B2 | 8/2002 | Denen |
| 6,491,233 B2 | 12/2002 | Nichols |
| 6,495,097 B1 | 12/2002 | Streit et al. |
| 6,501,052 B2 | 12/2002 | Cox et al. |
| 6,516,796 B1 | 2/2003 | Cox et al. |
| 6,536,746 B2 | 3/2003 | Watkins |
| 6,557,552 B1 | 5/2003 | Cox et al. |
| 6,568,390 B2 | 5/2003 | Nichols et al. |
| 6,602,475 B1 | 8/2003 | Chiao |
| 6,640,050 B2 | 10/2003 | Nichols et al. |
| 6,661,967 B2 | 12/2003 | Levine et al. |
| 6,666,909 B1 | 12/2003 | TeGrotenhuis et al. |
| 6,681,769 B2 | 1/2004 | Sprinkel, Jr. et al. |
| 6,681,998 B2 | 1/2004 | Sharpe et al. |
| 6,697,571 B2 | 2/2004 | Triplett et al. |
| 6,701,921 B2 | 3/2004 | Sprinkel, Jr. et al. |
| 6,701,922 B2 | 3/2004 | Hindle et al. |
| 6,715,487 B2 | 4/2004 | Nichols et al. |
| 6,752,327 B2 | 6/2004 | Martens, III et al. |
| 6,766,220 B2 | 7/2004 | McRae et al. |
| 6,772,757 B2 | 8/2004 | Sprinkel, Jr. |
| 6,786,427 B2 | 9/2004 | Schram et al. |
| 6,789,741 B2 | 9/2004 | Varanasi et al. |
| 6,792,199 B2 | 9/2004 | Levine et al. |
| 6,793,149 B2 | 9/2004 | Schramm et al. |
| 6,799,572 B2 | 10/2004 | Nichols et al. |
| 6,804,458 B2 | 10/2004 | Sherwood et al. |
| 6,843,430 B2 | 1/2005 | Boticki et al. |
| 6,854,470 B1 | 2/2005 | Pu |
| 6,871,792 B2 | 3/2005 | Pellizzari |
| 6,883,516 B2 | 4/2005 | Hindle et al. |
| 6,899,280 B2 | 5/2005 | Kotary et al. |
| 6,909,840 B2 | 6/2005 | Harwig et al. |
| 6,923,179 B2 | 8/2005 | Gupta et al. |
| 6,994,843 B2 | 2/2006 | Rabinowitz et al. |
| 7,040,314 B2 | 5/2006 | Nguyen et al. |
| 7,090,830 B2 | 8/2006 | Hale et al. |
| 7,100,841 B2 | 9/2006 | Ivey et al. |
| 7,117,867 B2 | 10/2006 | Cox et al. |
| 7,147,170 B2 | 12/2006 | Nguyen et al. |
| 7,367,334 B2 | 5/2008 | Faison, Jr. et al. |
| 2003/0132219 A1* | 7/2003 | Cox et al. ............ 219/486 |
| 2003/0218077 A1* | 11/2003 | Boticki et al. ......... 239/102.1 |
| 2004/0035409 A1* | 2/2004 | Harwig et al. ............ 126/96 |
| 2004/0065750 A1 | 4/2004 | Kotary et al. |
| 2004/0223917 A1* | 11/2004 | Hindle et al. ............ 424/45 |
| 2004/0265164 A1 | 12/2004 | Woo et al. |
| 2005/0143866 A1 | 6/2005 | McRae et al. |
| 2005/0205084 A1 | 9/2005 | Gupta et al. |
| 2006/0180143 A1 | 8/2006 | Lind et al. |
| 2007/0228071 A1* | 10/2007 | Kamen et al. ............ 222/52 |
| 2008/0251598 A1* | 10/2008 | Ross ..................... 239/44 |
| 2009/0194607 A1 | 8/2009 | Nichols et al. |
| 2009/0224064 A1 | 9/2009 | Brodbeck et al. |

FOREIGN PATENT DOCUMENTS

| | | |
|---|---|---|
| WO | WO 03/103387 A2 | 12/2003 |
| WO | WO 2004/094071 A1 | 11/2004 |
| WO | WO 2006/105154 A2 | 10/2006 |
| WO | WO 2009/027834 A2 | 3/2009 |

OTHER PUBLICATIONS

Utada, A.S., et al., Monodisperse Double Emulsions Generated from a Microcapillary Device, Science (vol. 38) Apr. 22, 2005 (pp. 537-541).

Notification Concerning Transmittal of International Preliminary Report on Patentability mailed Mar. 11, 2010 for International Application No. PCT/IB2008/003020.

U.S. Appl. No. 12/903,419, filed Oct. 13, 2010.

International Search Report and Written Opinion mailed Jan. 28, 2011 for International Application No. PCT/IB2010/002795.

International Preliminary Report on Patentability mailed Apr. 17, 2012 for PCT/IB2010/002795.

* cited by examiner

AIR FRESHENING DEVICE

CROSS REFERENCE TO RELATED APPLICATION

This application claims priority under 35 U.S.C. §119(e) to U.S. Provisional Patent Application No. 61/251,189, filed Oct. 13, 2009, the entire content of which is incorporated herein by reference.

SUMMARY

Provided is an air freshening device for generating a substantially deposition free vapor. The air freshening device includes a liquid supply operable to supply liquid material, a wick in fluid communication with the liquid supply, a conductive mesh material operable to retain the liquid material in interstices thereof; and a power supply operable to apply voltage across the mesh material, which acts as a heater, so as to heat the liquid material contained in interstices of the mesh material to a temperature sufficient to at least partially vaporize the liquid. In an embodiment, the vapor at least partially condenses to form an aerosol. The air freshening device is operable to substantially prevent deposition of the vaporized liquid material.

The conductive mesh material comprises at least one material selected from the group consisting of stainless steel, copper, copper alloys, porous ceramic materials coated with film resistive material, nickel-chromium alloys, and combinations thereof. Preferably, the conductive mesh material is about 200 to about 600 mesh. Most preferably, the conductive mesh material is about 400 mesh. The conductive mesh material is preferably formed with 0.001 diameter wire and can comprise one or more layers of woven wire.

Preferably, the wick comprises at least one polymer. Also preferably, the wick comprises a porous plastic wick.

In a preferred embodiment, the air freshening device can also include a capillary tube underlying the conductive mesh material. The capillary tube includes an inlet end in fluid communication with the wick, and an outlet end operable to deliver liquid to the mesh material by capillary action or direct the liquid material onto the mesh as a result of heating of the capillary tube. Preferably, the capillary passage has an internal diameter of about 0.05 mm to about 0.4 mm and a length of about 5 mm to about 100 mm, more preferably about 10 mm to about 40 mm. In an embodiment, the capillary passage comprises the interior of a stainless steel tube or the interior of a non-metallic tube.

In an embodiment, the power supply includes a supercapacitor that supplies an energy pulse to the heater. The air freshening device can also include control circuitry operable to deliver power from the power supply to the mesh in timed heating cycles such that the liquid material is at least partially vaporized after filling interstices of the mesh.

Also provided is a method for generation of vaporized material. The method includes drawing liquid material into a mesh material, and periodically applying voltage across the mesh material to rapidly heat the liquid material in interstices of the mesh material to a temperature sufficient to at least partially vaporize the liquid material such that the liquid material forms a vaporized material. The method can also include drawing the liquid material into a wick from a liquid supply, and drawing the liquid material into the interstices of the mesh material from the wick.

The method can also include a) generating vaporized material, b) cooling the mesh material, and c) repeating steps a) and b). Preferably, the mesh material is cooled in less than 10 seconds. Also preferably, vaporized material is generated about every 2 to 100 seconds. In the preferred embodiment, vaporized material is generated at least once an hour. The method can also include periodically applying voltage to the heater from a supercapacitor.

In an other embodiment, the method includes drawing liquid material into a capillary tube, applying voltage to the capillary tube to at least partially volatilize and expel the liquid material, catching remaining liquid material in the mesh material, and applying voltage to the mesh material to at least partially vaporize the liquid material contained in interstices of the mesh material by heating the liquid.

When formed, the vaporized liquid is discharged into ambient air.

DETAILED DESCRIPTION

Provided is a vapor and/or aerosol generator. Preferably, the vapor and/or aerosol generator is an air freshening device for generation of vaporized and/or aerosolized fragrance material. The air freshening device is operable to substantially prevent deposition of the vaporized liquid and provide a vapor and/or aerosol having a substantially uniform particle size.

Figure 1:
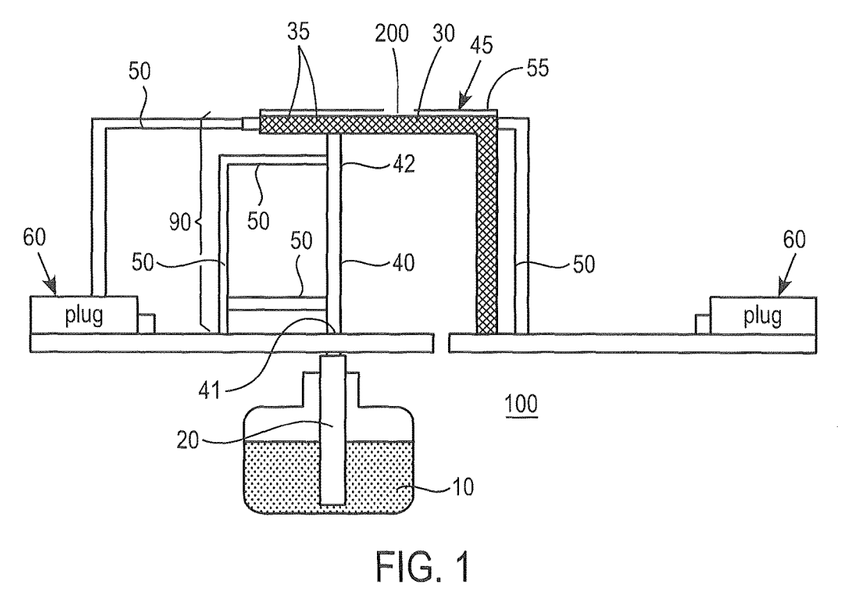
FIG. 1 is an illustration of a first embodiment of an air freshening device including a mesh material and a capillary tube.

As shown in FIG. 1, in a first embodiment, the air freshening device 100 includes a supply of liquid 10, a wick 20 in contact with the supply of liquid 10, a capillary tube 40 in fluid communication with the wick 20, a conductive mesh material 30 in communication with the capillary tube 40, and a power supply 60 operable to apply voltage across the mesh material 30. The liquid supply 10 is operable to supply liquid fragrance material to the wick 20, which is in fluid communication with a capillary tube 40. The capillary tube 40 underlies the mesh material 30 and transfers at least some of the liquid from the wick 20 to the mesh material 30 after voltage is applied to the capillary tube 40 in an amount sufficient to at least partially volatilize the liquid material contained in the capillary tube 40, which acts as a first heater. In a preferred embodiment, the capillary tube 40 contacts the mesh material 30. Once the liquid 10 has been delivered to the mesh material 30, the mesh material 30 retains the liquid material in interstices 35 thereof. The power supply 60 is then operable to rapidly heat the mesh material 30, which acts as a second heater. The liquid is rapidly heated to above its boiling point and is then released as a vapor. In an embodiment, the vapor at least partially condenses to form an aerosol. Preferably, the liquid is heated in less than about 1 second. Thus, the liquid material contained in the interstices 35 of the mesh material 30 is heated to a temperature sufficient to vaporize the liquid 10 once the mesh material 30 is heated.

In the preferred embodiment, the mesh material 30 and the capillary tube 40 are formed of conductive materials, and thus each acts as a heater. Preferably, the capillary tube 40 is heated before the mesh material 30 is heated. By heating the capillary tube 40, at least part of the liquid is volatilized and the remaining liquid is caught by the mesh material 30, which is then heated to vaporize the remaining liquid material.

In the preferred embodiment, the mesh material 30 is formed of a thermally and/or electrically conductive material. Suitable materials for forming the mesh material 30 are selected from the group consisting of stainless steel, copper, copper alloys, porous ceramic materials coated with film resistive material, Inconel® available from Special Metals Corporation, which is a nickel-chromium alloy, Nichrome®, which is also a nickel-chromium alloy, and combinations thereof.

Figure 2:
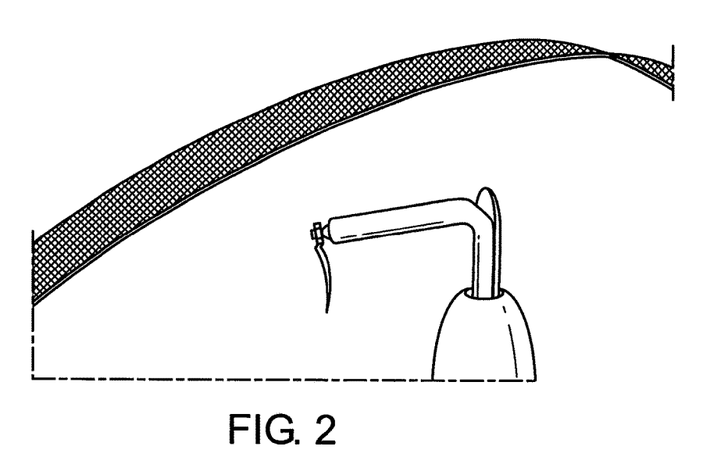
FIG. 2 is an enlarged view of the air freshening device of FIG. 1 showing the capillary tube and mesh material.

In use, once the capillary tube 40 is heated, the liquid material contained within a heated portion of the capillary tube 40 is volatilized and ejected out of the outlet 42. Any remaining liquid is propelled into the mesh material 30, where it is held in the interstices 35 of the mesh material 30. To prevent breakthrough of the liquid through the mesh material 30, a film 55 can be added to a top portion 45 of the mesh material 30. Voltage can then be applied to the mesh material 30 to rapidly heat the liquid 10 and vaporize any liquid in the interstices 35 of the mesh material 30. The vaporized material is released via an outlet 200 in the film 55, when present and on top of the mesh material 30, once pressure from the expanding liquid 10 forces the vaporized material out of the outlet 200. The outlet 200 can be positioned at an opening of the film 55. Alternatively, the outlet 200 can be located at the bottom of the mesh material 30. An enlarged view showing the relationship of the capillary tube 40 to the mesh material 30 is shown in FIG. 2.

In a preferred embodiment, a top portion 45 of the mesh material 30 can be at least partially covered with a film 55, such as a polyimide film. Suitable polyimide films include Kapton®, which is available from DuPont. Preferably, the film 55 is a non-porous film that prevents liquid material from breaking through the film 55.

In an embodiment, the vaporized material formed as described herein can at least partially condense to form an aerosol including particles. Preferably, the particles contained in the vapor and/or aerosol range in size from about 0.5 micron to about 4 microns, preferably about 1 micron to about 4 microns. In the preferred embodiment, the vapor and/or aerosol has particles of about 3.3 microns or less. Also preferably, the particles are substantially uniform throughout the vapor and/or aerosol.

The particle size can be analyzed using a Spraytec® detector having the following settings and conditions: a 300 mm lens, a particulate refractive index of 1.40+0.00i, a dispersant refractive index of 1.00, a path length of 25.4000 mm, a particle density of 0.90 gm/cc, a mesh factor of 0%, a wavelength of 632.8 mm, a beam diameter of 10.00 mm and a transmission of 98.719543457%. When tested, the volume median diameter particle values are as follows: dv(10) of about 0.198 micron (dv(10) is the particle size below which 10% of the volume of particles exist), dv(50) of about 0.598 micron (dv(50) is the particle size below which 50% of the volume of particles exist) and dv(90) of about 3.300 microns (dv(90) is the particle size below which 90% of the volume of particles exist).

In the preferred embodiment, the mesh material 30 can range in size from about 200 mesh to about 600 mesh. In the preferred embodiment, the mesh material 30 is about 400 mesh and includes small voids/interstices 35 between the wires that form the mesh material 30. Preferably, the mesh material 30 is formed with 0.001 inch diameter wire, such as wire available from Smallparts, Inc. Preferably, the wire is solid and not hollow and/or tube-like. Also preferably, the mesh material 30 has a criss-cross, checkerboard type pattern with interstices 35 therein. In the preferred embodiment, the mesh material 30 is a single, flat layer of mesh material.

In the preferred embodiment, the mesh material 30 is formed as a rectangle (shown in FIG. 3) having dimensions ranging from about 2.0 mm to about 10 mm in width and about 15 mm to about 40 mm in length. In the preferred embodiment, the mesh material 30 has dimensions of about 2.75 mm in width and about 23 mm in length. Preferably, the mesh material 30 achieves an electrical resistance ranging from about 0.1 Ohm to about 50 Ohms, more preferably about 0.8 Ohm to about 2.5 Ohms. In the preferred embodiment, the mesh material 30 has an electrical resistance of about 2.0 Ohms. Preferably, the size of the mesh material 30, and thus the interstices 35, will determine the amount of vaporized material released therefrom.

Figure 4:
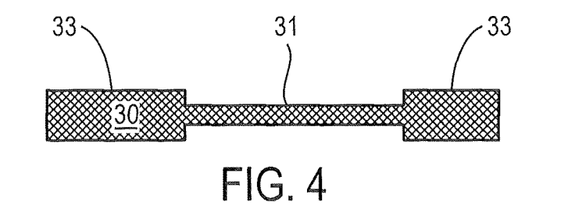
FIG. 4 is an illustration of a second embodiment of a mesh material.
Figure 5:
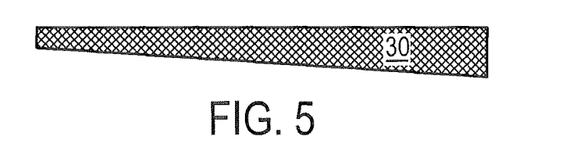
FIG. 5 is an illustration of a third embodiment of a mesh material.

The mesh material 30 can be formed having other geometries as shown in FIGS. 4 and 5. As shown in FIG. 4, the mesh material 30 can be formed in a barbell type shape having ends 33 and a narrow central region 31. As shown in FIG. 5, the mesh material 30 can be formed in a trapezoid shape.

Figure 3:
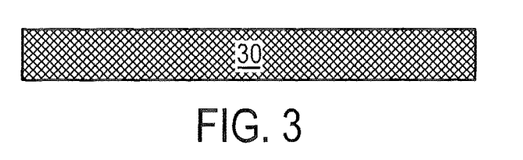
FIG. 3 is an illustration of a first embodiment of a mesh material.

Not wishing to be bound by theory, it is believed that by changing the geometry of the mesh material 30, the temperature profile of the heater (mesh material) can be altered. Altering the temperature profile of the heater can result in the use of less energy for forming the vapor. For example, the rectangular shaped mesh material 30 shown in FIG. 3 is substantially uniform in temperature across the length and width of the heater. In contrast, a barbell shaped mesh material 30, as shown in FIG. 4, is configured such that the heating can be preferentially focused in the central region 31, leaving the ends 33 of the mesh material 30 cooler. Thus, the barbell shaped mesh material 30 provides an efficient heating system where heat is generated when the mesh material 30 contacts the wick at a liquid retention zone 300 (shown in FIG. 7), and thus where the liquid is contained in the interstices 35 of the mesh material 30. The trapezoid shape of FIG. 5, can be used to provide a means for increasing the temperature from right to left thereby allowing for release of a vapor over time. By pairing different wick geometries with different heater geometries, an efficient rapid heater design can be achieved.

Figure 6:
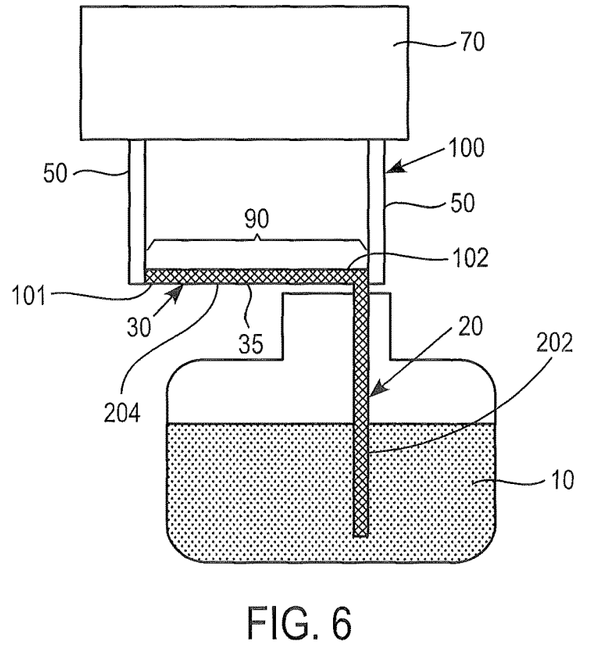
FIG. 6 is an illustration of a second embodiment of an air freshening device including a mesh material.
Figure 7:
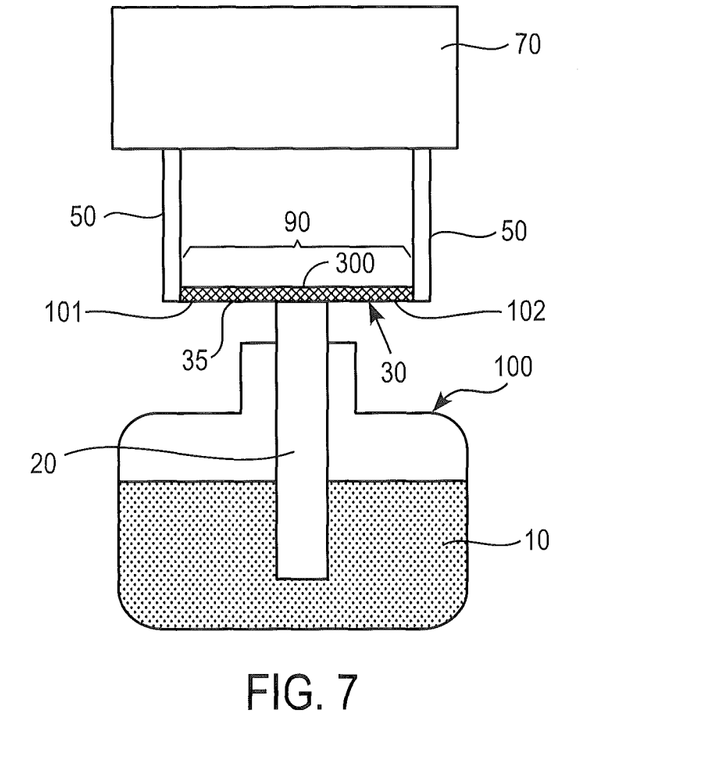
FIG. 7 is an illustration of a third embodiment of an air freshening device including a mesh material.

Preferably, at least two electrical leads 50 are bonded to the mesh material 30. In the preferred embodiment, the at least two electrical leads 50 are brazed to the mesh material 30. Preferably, one electrical lead 50 is brazed to a first end 101 of the mesh material 30 and a second electrical lead 50 is brazed to a second end 102 of the mesh material 30, as shown in FIGS. 6 and 7.

In a preferred embodiment, the wick 20 is submerged in the supply of liquid 10. While the wick 20 can be made of a variety of materials, porous plastic wicks are preferred. An example of a porous plastic wick is a wick 20 composed of ultra high molecular weight, high density polyethylene (HDPE). Such wicks 20 are generally made of blends of HDPE in particle form, and the blends are developed to meet the target pore characteristics of the wick 20. Preferably, the solubility parameter of the polymer is significantly different from that of the liquid material, which prevents the wick 20 from swelling or other changes that can lead to a change in the pore size and porosity of the wick 20.

Preferably, the wick 20 is positioned so as to be remote from the heat source so as to avoid damage to the wick 20. However, in a preferred embodiment, the wick 20 contacts the mesh material 30. Also preferably, the wick 20 is cylindrical and has a diameter of about 4 mm to about 5 mm. In the preferred embodiment, the diameter of the wick is about 4.8 mm.

In the preferred embodiment, the supply of liquid 10 includes liquid fragrance material, which may be any suitable liquid fragrance material that can be delivered to the mesh material 30 and/or capillary tube 40 for generation of vapor and/or aerosol. For example, the liquid material may be any commercially available liquid material suitable for use in commercial vaporized and/or aerosolized fragrance generators. The liquid material is preferably aqueous based, alcohol based, such as, for example, methanol, or propylene glycol based. In an alternative embodiment, the air freshening device 100 can be used as a vapor and/or aerosol generator for use with liquid supplies including, without limitation, insecticides, disinfectants, deodorizers, lubricants, fumigants, pest and weed control agents and combinations thereof.

In an embodiment, as shown in FIG. 1, an inlet end 41 of a capillary tube 40 contacts the wick 20 and transports the liquid from the wick 20 through the capillary tube 40 by capillary action. The capillary tube 40 preferably has an internal diameter of 0.01 to 10 mm, preferably 0.05 to 1 mm, and more preferably 0.05 to 0.4 mm. For example, the capillary tube can have an internal diameter of about 0.05 mm. Capillary tubes having a smaller diameter are more preferred due to the heat transfer to the fluid because the shorter the distance to the center of the fluid the less the amount of energy and time to vaporize. Alternatively, the capillary tube has an internal cross sectional area of $8 \times 10^{-5}$ to 80 mm$^2$, preferably 0.002 to 0.8 mm$^2$, more preferably 0.002 to 0.05 mm$^2$. For example, the capillary tube can have an internal cross sectional area of about 0.002 mm$^2$.

The capillary tube 40 may have a length of about 5 mm to about 100 mm, more preferably about 10 mm to about 40 mm, e.g., about 25 mm or about 50 mm. The capillary tube 40 preferably is a stainless steel capillary tube 40, which serves as a second heater via electrical leads 50 attached thereto for passage of direct or alternating current along a length of the tube 40. Thus, the stainless steel tube 40 is heated by resistance heating. The stainless steel tube 40 is preferably circular in cross section. The tube 40 may be of tubing suitable for use as a hypodermic needle of various gauges. For example, a 32 gauge needle has an internal diameter of 0.11 mm and a 26 gauge needle has an internal diameter of 0.26 mm.

However, the capillary tube 40 may be any electrically conductive material capable of being resistively heated, while retaining the necessary structural integrity at the operating temperatures experienced by the capillary tube 40, and which is sufficiently non-reactive with the liquid material. Such materials include, but are not limited to stainless steel, INCONEL, metal composites, or other metals and alloys.

In an additional embodiment, the capillary tube 40 may be a non-metallic tube such as, for example, a glass tube. In such an embodiment, the heater is formed of a conductive material capable of being resistively heated, such as, for example, stainless steel, NICHROME or platinum wire, arranged along the glass tube. When the heater arranged along the glass tube is heated, liquid material in the capillary tube 40 is heated to a temperature sufficient to at least partially volatilize liquid material in the capillary tube 40.

The power supply 60 for applying a voltage may include a voltage source and at least two electrical leads 50 as described in commonly assigned U.S. Patent Application Publication No. 2009/0194607, filed Aug. 28, 2008, the entire content of which is incorporated herein by reference. At least two electrical leads 50 are connected to the mesh material 30 and at least two electrical leads 50 are connected to the capillary tube 40. Preferably, the capillary tube 40 includes a first voltage source and the mesh material 30 includes a second voltage source. In one embodiment, the voltage source can be a direct current battery. The battery can be a rechargeable battery. In another embodiment, the voltage source provides an alternating current. The air freshening device 100 can be connected to the voltage source in a tethered and/or untethered manner. In the preferred embodiment, the electrical leads 50 are attached to spaced apart locations along the mesh 30 and/or capillary tube 40 to supply power that resistively heats the mesh material 30 and/or capillary tube 40. The capillary tube 40 and the mesh material 30 can be powered by the same or different voltage source.

The power supply 60 preferably delivers a pulse of power to the mesh material 30 and/or capillary tube 40 via the electrical leads 50. The voltage chosen determines the amount of energy that will be used to heat the mesh material 30 and/or capillary tube 40 in each pulse. The energy transferred to the mesh material 30 and/or capillary tube 40 from the voltage source is governed by Ohm's Law.

$$V(\text{voltage}) = I(\text{current}) \cdot R(\text{resistance}) \tag{1}$$

$$\text{Power} = V \cdot I = V^2/R \tag{2}$$

Preferably, the liquid supply 10 is vented. The liquid supply 10 may include a wick 20 that delivers liquid material from the liquid supply to the inlet of the capillary tube 40 via capillary action. Preferably, the wick material contains numerous pores, and these pores act as capillary passages, which cause the liquid material to be drawn into them and then into an inlet of the capillary tube 40.

Not wishing to be bound by theory, it is believed that manipulation of parameters of the air freshening device, such as, for example, the internal diameter of the capillary tube 40, geometry of the wick 20 and/or mesh material 30 and/or heat transfer characteristics of the material defining the capillary tube 40 and/or mesh material 30, can be selected to control heater temperature and mass median particle diameter. Furthermore, choice of the liquid material can affect heater temperature and mass median particle diameter of the vaporized material.

The air freshening device 100 may be a small portable device including a power supply 60 in the form of a battery. In a second embodiment, the power supply 60 may be an alternating current (AC) source, such as an AC outlet and the air freshening device can include a converter if desired to convert the AC to direct current supplied to the heater. The air freshening device 100 may be operated by control circuitry 70 (shown in FIGS. 6 and 7) operable to deliver power from the power supply 60 to the heater (mesh material 30 and/or capillary tube 40) in timed heating cycles. Thus, the control circuitry 70 controls the application and/or frequency of voltage across the mesh material 30 and/or capillary tube 40 in order to vaporize the liquid material.

The control circuitry 70 may automatically control the frequency of repeated pulsed vaporization of liquid material. Alternatively, the frequency of repeated pulsed generation of vaporized material may be preset or manually set, with the control circuitry 70 controlling generation of vaporized material according to the preset or manually selected frequency. If desired, the control circuitry 70/power supply 60 may include primary and/or secondary cells, preferably primary cells, capacitors including supercapacitors, charge pumps, and combinations thereof. Use of a supercapacitor may extend battery life and/or allow for use of fewer or smaller batteries.

It is desirable for an air freshening device 100 to produce a particle size as small as possible. Stokes' Law predicts the settling velocity of small spheres in fluid such as air or water. The equation for Stokes' Law is: $w=2(\rho_p-\rho_f)gr^2/9\mu$ where w is the settling velocity, $\rho$ is density (the subscripts p and f indicate particle and fluid respectively), g is the acceleration due to gravity, r is the radius of the particle and $\mu$ is the dynamic viscosity of the fluid. Table 1 shows the settling velocity in air for a series of particle sizes from 1-50 micron.

TABLE 1

| Particle Size Diameter Micron | Settling Velocity cm/sec |
| --- | --- |
| 1 | 0.003 |
| 5 | 0.07 |
| 10 | 0.3 |
| 50 | 7.4 |

During the power cycle, any tendency for liquid to be drawn into the heated zone 90, including the capillary tube 40 and/or the mesh material 30, is interrupted by the heating of liquid already within the heated zone 90, and preferably sufficient energy is applied along the heated portion of the capillary tube 40 and/or mesh material 30 to fully evacuate the liquid along the heated zone 90 by conclusion of the power cycle. The requisite energy is readily resolved by knowing the volume and therefore the mass of liquid contained along the heated zone 90 of the capillary tube 40 and/or mesh material 30, the latent heat of that mass plus the specific heat of the volume/mass, with the addition of approximately 25% margin to accommodate variations and losses. Such operation assures that the liquid is fully evacuated and does not remain at any location along the heated zone 90 of the capillary tube 40 and/or mesh material 30, so that feeding of liquid to the heated zone 90 can resume after completion of the power cycle and is not blocked. The time between power cycles is preferably greater than the time required for capillary action to draw liquid from the liquid supply 10 and refill the heated zone 90.

Figure 9:
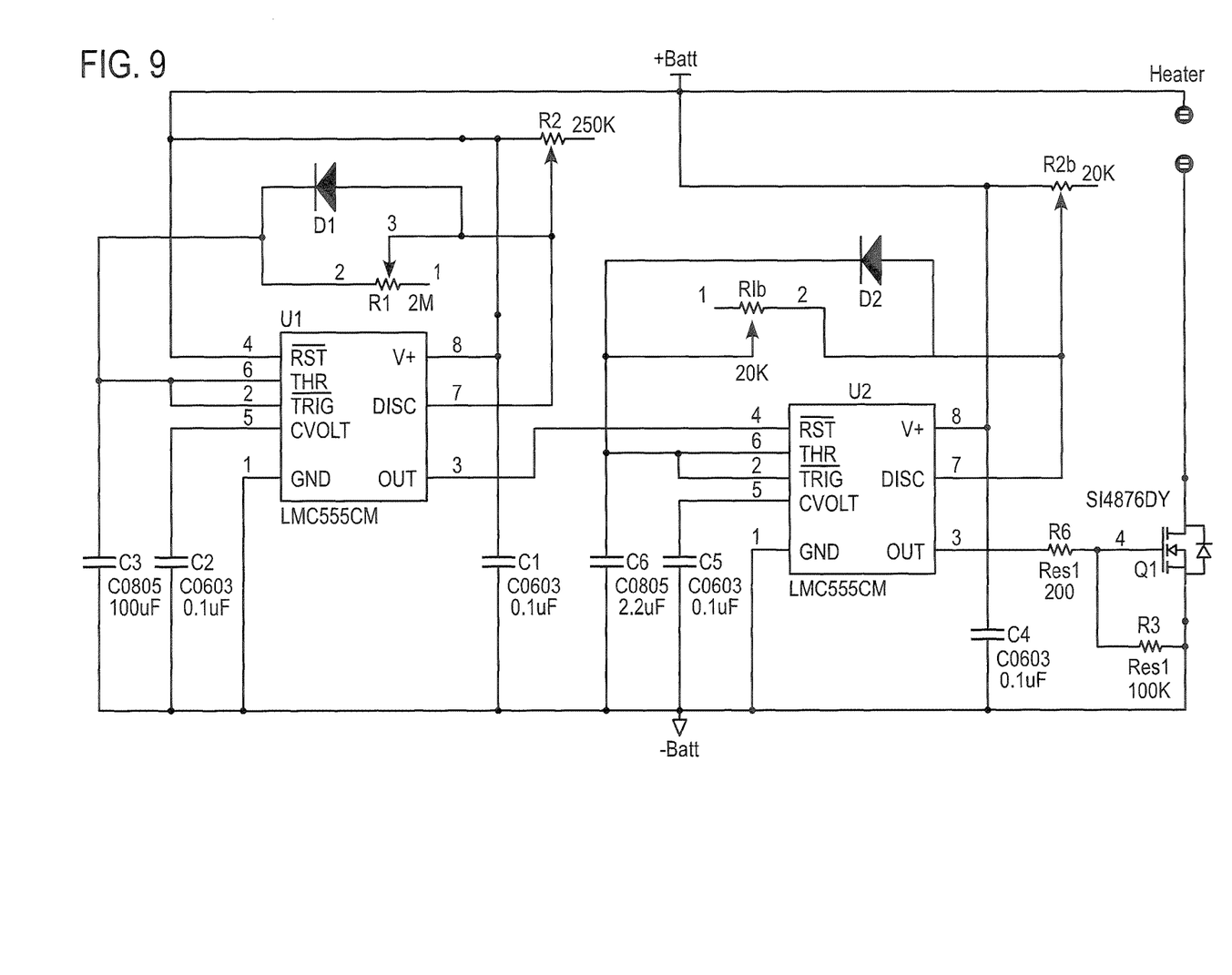
FIG. 9 is schematic of a first exemplary control circuit for use with the air freshening device.

FIG. 9 is schematic of a basic 555 timer circuit for use with the air freshening device 100. Two resistive potentiometers (POT) are used to set the timing of the square wave pulse signal. The signal is sent to a field-effect transistor (FET) that connects the power supply to the heater. Alternatively, programmable circuits, such as those described above can be used.

Figure 10:
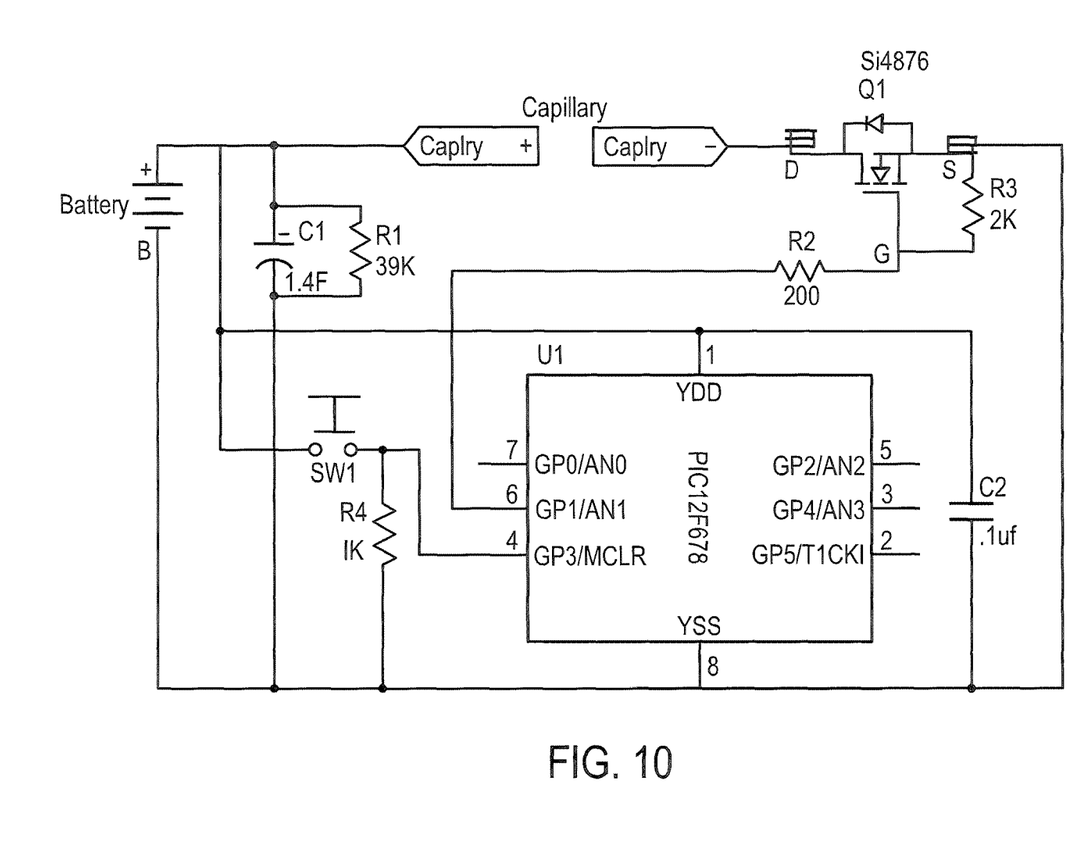
FIG. 10 is a schematic of a second exemplary control circuit for use with the air freshening device.

FIG. 10 is a schematic of exemplary control circuitry, including a heater for the capillary tube and/or mesh material ("capillary" in FIG. 10) and electrical leads ("Caplry +" and "Caplry −"). These leads can be attached at spaced apart locations along a stainless steel capillary tube and/or mesh material in which liquid material is heated by pulsing power through the leads. While the control circuitry may be powered by one or more batteries, such as AA cells, the control circuitry is powered by one battery B. The control circuitry preferably comprises a master power switch SW1, as well as a microcontroller U1, such as a PIC12F675, manufactured by Microchip. The microcontroller U1 has unutilized outputs 2, 3, 5, 7, which may be employed depending on the complexity of the control circuitry. The timing of energizing the heater of the air freshener is preferably set by an internal clock of the microcontroller. For adjustable timing, a pushbutton switch can be pressed one or more times to set the time interval between vapor delivery. An indicator LED displaying information such as the set time interval may also be controlled by the microcontroller. The field effect transistor Q1, such as, for example, Si4876, is used to switch power to the capillary heater under control of the microcontroller. While energy can be directly delivered to the heater by the battery, the control circuitry has a power supply that includes a supercapacitor C1, which supplies energy as an energy pulse to the capillary heater, i.e., the supercapacitor discharges a pulse of energy to the heater sufficient to volatilize liquid fragrance material in the capillary tube and/or vaporize the liquid fragrance material mesh material. The microcontroller U1 is preprogrammed or manually set for a timing cycle whose duration is shorter than time required for the supercapacitor C1 to recharge. Additional elements of the control circuitry include a capacitor C2 and resistors R1, R2, R3, R4.

FIG. 6 shows a second embodiment of an air freshening device 100 including a mesh material 30 which forms both the wick 20 and a heater. The mesh material 30 can form an L-shaped piece, with one portion at least partially submerged in a liquid supply 10 and a second portion perpendicular to the submerged portion and not in contact with the liquid supply 10. Preferably, the mesh material is flat, has a criss-cross pattern, and is about 400 mesh to about 600 mesh. The portion not in contact with the liquid supply 10 forms a heated portion 204 operable to vaporize liquid material contained in the interstices 35 of the mesh material 30. The submerged portion forms an unheated portion 202 that acts as a wick to transfer liquid 10 from the liquid supply to the heated portion 204. Liquid is contained in the interstices of the wick 20 and then pushed into interstices of portions of the unheated portion 202 in contact with the interstices of the unheated portion 202 containing liquid. Liquid is then heated to a temperature sufficient to vaporize the liquid contained in interstices 35 of the mesh material 30. Electrical leads 50 are attached to the heated portion 204 of the mesh material 30 at a first end 101 and a second end 102 of the heated portion 204.

FIG. 7 shows a third embodiment of an air freshening device 100 including a mesh material 30 in contact with a wick 20, which is submerged in a supply of liquid 10. Preferably, the mesh material 30 is a single, thin layer of wire mesh that lays on top of and contacts the tip of the wick 20. The mesh material 30 is removable from the wick 20, and thus is not permanently connected to or otherwise affixed to the wick 20. In other embodiments, the mesh material 30 can be wrapped around the end of the wick 20 and/or the mesh material 30 can contact the top and sides of the wick 20. Preferably, the wick 20 is a porous, polymeric wick as described above. The mesh material 30 contacts the wick such that the liquid is transferred to interstices 35 of the mesh material 30 where the mesh material 30 contacts the wick 20. Preferably, capillary action is not used to draw liquid into the interstices 35 of the mesh material 30. Instead, the liquid is transferred to the interstices by contact therewith. Electrical leads 50 are attached to a first end 101 and a second end 102 of the mesh material 30. A heated zone 90 is formed between the electrical leads 50 when voltage is applied. The air freshening device 100 may be operated by control circuitry 70 operable to deliver power from the power supply to the heater. The power supply is operable to apply voltage across the mesh so as to heat the liquid material contained in interstices of the mesh material to a temperature sufficient to vaporize the liquid. The vaporized material is then released through an outlet on the top of the mesh.

In the preferred embodiment, the liquid contained in interstices of the mesh material is vaporized in less than about 1 second, more preferably in less than about 0.5 second, and most preferably in less than about 0.2 second.

The following examples are exemplary and are not meant to limit any aspect of the embodiments disclosed herein.

EXAMPLE 1

An air freshening device was formed including a mesh material made of stainless steel wires having a diameter of about 0.001 inch. The mesh material has dimensions of about 2.75 mm by about 23 mm so as to provide a heater that does not draw excessive current and covers a majority of the top of a polymeric wick. The mesh material has a theoretical resistance of about 0.793 Ohm and a measured resistance of about 0.84 Ohm. On each end of the mesh material, an electrical lead was brazed across the width of the mesh material. The heater assembly was attached to a pulse width modulation 555 timer circuit driven with 5 volts. The 555 timer circuit was set to cycle on for 0.14 seconds, every 7 seconds. The 555 timer circuit output triggered a field effect transistor to apply 5 volts across the heater. The heater was mounted on top of the polymeric wick that extended into a reservoir of liquid fragrance material. When the mesh heater contacted the top of the wick, liquid drawn by capillary action to the of the top of the wick filled the interstices of the mesh material that was in contact with the wick. No capillary action moved liquid along the length of the heater. The circuit was turned on and fragrance output was measured at the end of an hour. The liquid fragrance output was about 114 mg/hr.

The air freshening device output of Example 1 correlates with the theoretical calculation of interstitial area of the heater over the wick and a liquid film thickness within the interstices of about 0.0015 inch. This correlation further supports that capillary action is not occurring along the length of the mesh material. In addition, no signs of degradation or melting of the wick was observed.

Additionally provided is a method for generation of vaporized material, which includes drawing liquid material into an inlet 41 of a capillary tube 40 only via capillary action. Liquid enters interstices 35 of the mesh material 30 by contacting the mesh material 30 and the wick 20. The method also includes periodically applying voltage across the mesh material 30 and capillary tube 40 in a first embodiment, or to the mesh material 30 alone in a second embodiment, to heat liquid material in the mesh material 30 and/or capillary tube 40 to a temperature sufficient to at least partially vaporize the liquid material.

In the preferred embodiment, when both a capillary tube 40 and a mesh material 30 are used, liquid is drawn into the capillary tube 40 by capillary action. Then, voltage is applied to the capillary tube 40 to at least partially volatilize the liquid material contained therein and expel the fragrance material from the outlet 42 of the capillary tube and thus the device 100. Any remaining liquid expelled along with the fragrance material is caught by the mesh material 30 where the liquid is contained in interstices 35 thereof. Then, voltage is applied to the mesh material 30 to rapidly heat the mesh material 30 and cause the liquid material caught by the mesh material 30 and contained in the interstices 35 thereof to form a vapor. Thus, both the capillary tube 40 and the mesh material 30 are heaters which have individual circuits including two electrical leads and a power supply.

After the voltage is applied across a mesh and/or capillary tube, the liquid material is vaporized and the mesh and/or capillary tube cools and are refilled. The mesh and/or capillary tube refill time is a function of the length of the mesh material and/or length and diameter of the capillary tube as well as the properties of the wick and liquid material. For example, for a 25 mm long, 0.15 mm internal diameter capillary tube, refill can occur in less than 10 seconds. Once the capillary tube and/or mesh material cools, more liquid material is drawn into the capillary tube and interstices of the mesh material are filled with liquid material where the mesh material contacts the wick. The control circuitry can activate periodically to apply voltage across the mesh and/or capillary tube to heat liquid material in the interstices of the mesh and/or contained in the capillary tube. Accordingly, a method for repeated pulsed generation of vaporized material includes vaporizing liquid material, cooling the mesh and/or capillary tube, and repeating the filling and vaporization steps.

The frequency of repeated pulsed generation of vaporized material is limited by the mesh and/or capillary tube refill time. Thus, depending on the length of the mesh material and the length and diameter of the capillary tube and the liquid material, vaporized fragrance material may be generated as frequently as every 2 to 100 seconds, perhaps at least once a minute, or less frequently, such as, for example, at least once an hour or at least once a day. In order for the mesh and/or capillary tube to be effectively refilled, substantially all of the liquid material contained in the mesh and/or capillary tube is driven out of the mesh and/or capillary tube by heating, thus providing a substantially dry mesh and/or capillary tube.

To determine the deposition of vaporized liquid material product by the air freshening device of FIG. 1 and FIG. 2 as compared to air freshening devices including only a capillary tube and no mesh material, air freshening devices were prepared and filled with the same liquid material. Then, each air freshening device was heated every 15 seconds for about one hour. A piece of thermal paper was placed under and at the outlet end of each air freshening device. When exposed to liquid droplets, the thermal paper shows a contrast in color where liquid has contacted the thermal paper. The results are shown in FIG. 8A, FIG. 8B and FIG. 8C.

Figure 8A:
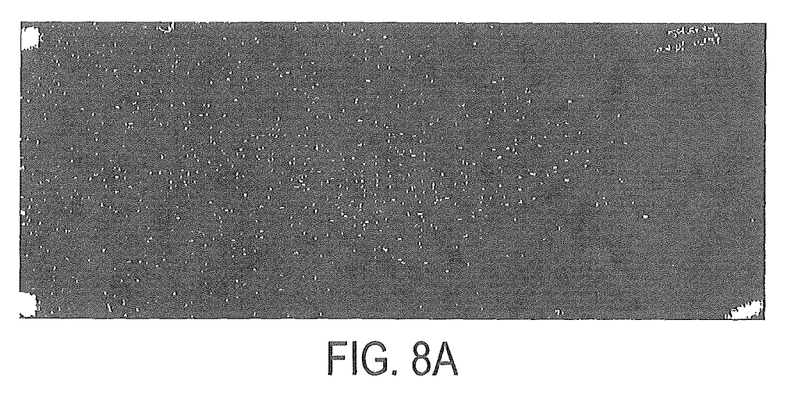
FIGS. 8A, 8B and 8C are photographs showing the deposition created by an air freshening device including only a capillary tube, an air freshening device including a capillary tube and a mesh as described herein, and an air freshening device including only a mesh as described herein.
Figure 8B:
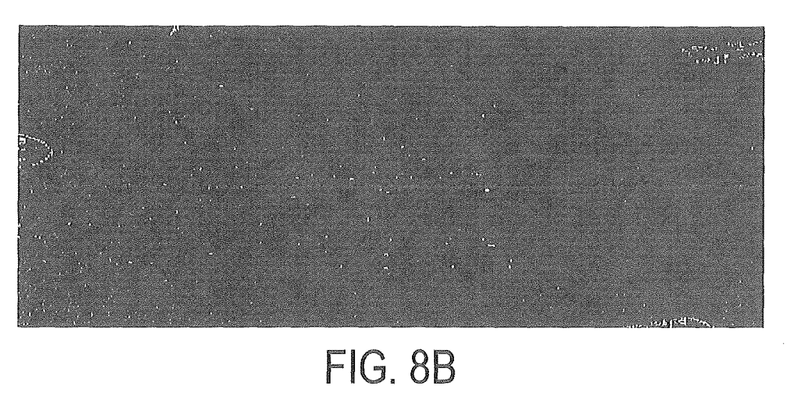
Figure 8C:
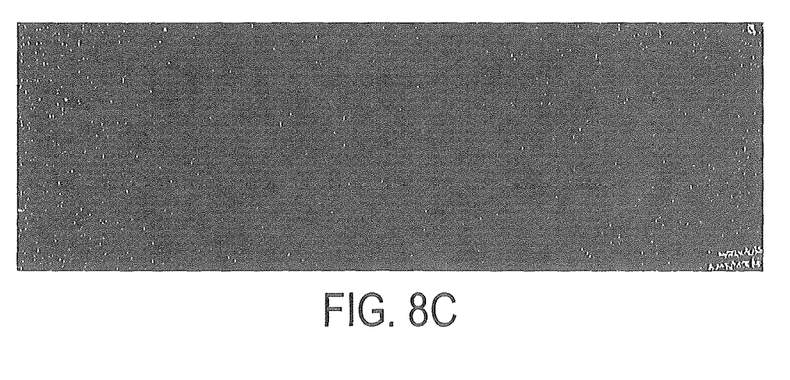

FIG. 8A shows substantial deposition of liquid material by air freshening device including only a heated capillary tube and no mesh material. FIG. 8B shows substantially less deposition by an air freshening device including a heated capillary tube and heated mesh material as compared to an air freshening device including only a capillary tube. FIG. 8C shows the least deposition occurs as a result of using an air freshening device including only a heated mesh material without a heated capillary tube.

In this specification, the word "about" is often used in connection with a numerical value to indicate that mathematical precision of such value is not intended. Accordingly, it is intended that where "about" is used with a numerical value, a tolerance of 10% is contemplated for that numerical value.

Moreover, when the words "generally" and "substantially" are used in connection with geometric shapes, it is intended that precision of the geometric shape is not required but that latitude for the shape is within the scope of the disclosure. When used with geometric terms, the words "generally" and "substantially" are intended to encompass not only features which meet the strict definitions but also features which fairly approximate the strict definitions.

While the foregoing describes in detail an apparatus and method for forming a vaporized fragrance material, it will be apparent to one skilled in the art that various changes and modifications may be made to the disclosed apparatus and methods and further that equivalents may be employed, which do not materially depart from the spirit and scope of the invention. Accordingly, all such changes, modifications, and equivalents that fall within the spirit and scope of the invention as defined by the appended claims are intended to be encompassed thereby.

We claim:

1. An air freshening device comprising:
a liquid supply operable to supply liquid material;
a conductive mesh material operable to retain the liquid material in interstices thereof, wherein the conductive mesh material forms a wick in contact with liquid in the liquid supply and a mesh heater not in contact with the liquid supply; and
a power supply operable to apply voltage across a heated portion of the mesh heater so as to heat the liquid material contained in interstices of the mesh material to a temperature sufficient to vaporize the liquid,
wherein the air freshening device is operable to substantially prevent deposition of the vaporized liquid material.

2. The air freshening device of claim 1, wherein the conductive mesh material comprises at least one material selected from the group consisting of stainless steel, copper, copper alloys, porous ceramic materials coated with film resistive material, nickel-chromium alloys, and combinations thereof.

3. The air freshening device of claim 1, wherein the conductive mesh material is about 200 to about 600 mesh.

4. The air freshening device of claim 1, wherein the conductive mesh material is about 400 mesh.

5. The air freshening device of claim 1, wherein the conductive mesh material is formed with 0.001 inch diameter wire.

6. The air freshening device of claim 1, wherein the heater comprises a section of the conductive mesh material located between two spaced apart electrical leads.

7. The air freshening device of claim 1, wherein the air freshening device is operable to vaporize liquid material to form an aerosol having a substantially uniform particle size, and wherein the aerosol has particles ranging in size from about 0.5 micron to about 4 microns or about 1 micron to about 4 microns.

8. An air freshening device comprising:
a liquid supply operable to supply liquid material;
a wick in contact with liquid in the liquid supply;
a conductive mesh material operable to retain the liquid material in interstices thereof;
a capillary tube underlying the conductive mesh and having an inlet and an outlet, said capillary tube operable to draw liquid material from the wick via capillary action and supplying the liquid material to the conductive mesh; and
a power supply operable to apply voltage across a capillary heater comprising the capillary tube so as to heat the liquid material contained in the capillary tube to a temperature sufficient to at least partially volatilize the liquid within the capillary tube and across a mesh heater comprising the conductive mesh material so as to heat the liquid material contained in interstices of the mesh material to a temperature sufficient to vaporize the liquid,
- wherein the air freshening device is operable to substantially prevent deposition of the vaporized liquid material.

9. The air freshening device of claim 8, wherein the capillary tube has an internal diameter of about 0.05 to 0.4 mm and a length of about 5 mm to about 100 mm or about 10 mm to 40 mm.

10. The air freshening device of claim 8, wherein the capillary tube comprises a stainless steel tube or a non-metallic tube.

11. The air freshening device of claim 8, wherein the wick comprises at least one polymer.

12. The air freshening device of claim 11, wherein the wick comprises a porous plastic wick.

13. The air freshening device of claim 1, wherein the power supply includes a supercapacitor that supplies an energy pulse to the heater.

14. The air freshening device of claim 1, further comprising control circuitry operable to apply voltage from the power supply to the mesh in timed heating cycles such that the liquid material is at least partially vaporized after filling of a liquid retention zone of the mesh.

15. The air freshening device of claim 1, wherein the liquid material comprises an aqueous liquid fragrance material.

16. The air freshening device of claim 1, wherein the liquid material is vaporized in less than about 1 second via heating.

17. A method for generation of vaporized material comprising:
- drawing liquid material into a wick from a liquid supply;
- using the wick to deliver the liquid material into interstices of a mesh heater, wherein the wick and the mesh heater are formed from a conductive mesh material; and
- periodically applying voltage across a heated portion of the mesh heater to heat the liquid material in the interstices of the mesh material to a temperature sufficient to heat the mesh material and at least partially vaporize the liquid material such that the liquid material is driven out of the interstices of the mesh material and forms a vaporized material.

18. A method for repeated pulsed generation of vaporized material comprising:
- a) generating vaporized material according to the method of claim 17;
- b) cooling the mesh material; and
- c) repeating steps a) and b).

19. The method of claim 18, comprising cooling the mesh material in less than 10 seconds.

20. The method of claim 18, comprising generating vaporized material every 2 to 100 seconds.

21. The method of claim 18, comprising generating vaporized material at least once an hour.

22. The method of claim 18, comprising periodically applying voltage from a supercapacitor to the mesh material.

23. The air freshening device of claim 1, wherein a portion of the wick is at least partially submerged in the liquid supply.

24. The air freshening device of claim 1, wherein the mesh material is an L-shaped piece, with one portion at least partially submerged in the liquid supply and a second portion perpendicular to the submerged portion and not in contact with the liquid supply.

* * * * *